(12) United States Patent
Guiraud et al.

(10) Patent No.: US 6,307,115 B1
(45) Date of Patent: Oct. 23, 2001

(54) METHOD FOR PURIFYING PENTAFLUOROETHANE

(76) Inventors: Emmanuel Guiraud, 14 Rue du 11 Novembre, 62930 Saint Genis Laval; Cathy Descamps, 70 Ronte de Saint Romain, 69450 Saint Cyr au Mont d'or, both of (FR)

( * ) Notice: Subject to any disclaimer, the term of this patent is extended or adjusted under 35 U.S.C. 154(b) by 0 days.

(21) Appl. No.: 08/875,945
(22) PCT Filed: Feb. 6, 1996
(86) PCT No.: PCT/FR96/00196
  § 371 Date: Nov. 13, 1997
  § 102(e) Date: Nov. 13, 1997
(87) PCT Pub. No.: WO96/24569
  PCT Pub. Date: Aug. 15, 1996

(30) Foreign Application Priority Data
Feb. 7, 1995 (FR) .................................................. 95 01381

(51) Int. Cl.$^7$ .................................................. C07C 17/38
(52) U.S. Cl. ........................................... 570/178; 570/180
(58) Field of Search ...................................... 570/178, 180

(56) References Cited

U.S. PATENT DOCUMENTS 5,200,431  4/1993  Dattani et al. .
6,179,967 * 1/2001  Nishimura et al. .................. 570/178

FOREIGN PATENT DOCUMENTS 472391      2/1992  (EP) .
WO 95/21147 8/1995  (WO) .

OTHER PUBLICATIONS

Research Disclosure, vol. 360, 1994, Havant, pp. 191–193 "Methods for Separating Chloro–Carbons fro Hydrofluoro-alkanes".

* cited by examiner

*Primary Examiner*—Alan Siegel
(74) *Attorney, Agent, or Firm*—Smith, Gambrell & Russell LLP

(57) ABSTRACT

The invention relates to the purification of pentafluoroethane (F125) containing chloropentafluoroethane (F115) by liquid/liquid extraction or by extractive distillation.

Perchloroethylene is used as extraction agent.

4 Claims, 5 Drawing Sheets

METHOD FOR PURIFYING PENTAFLUOROETHANE

This application is a 371 of PCT/FR96/00196 filed Feb. 6, 1996.

FIELD OF THE INVENTION

The invention relates to the purification of pentafluoroethane (F125) containing chloropentafluoroethane (F115) and relates more particularly to a purification process in which the F115 is removed by liquid/liquid extraction or by extractive distillation and readily recovered so that it can be converted subsequently into products that are harmless to the earth's atmosphere.

BACKGROUND OF THE INVENTION

Pentafluoroethane is one of the possible replacements for chlorofluorocarbons (CFC), which are the subject-matter of the Montreal protocol and are characterized by an exceptionally long lifetime which allows them to reach the upper layers of the atmosphere and thus play a part, under the influence of UV radiation, in destroying the ozone layer. It is thus obvious that, as a function of the various production processes, their replacements should contain only traces of these CFCs.

The replacements are generally obtained either by appropriate fluorination methods, which are not highly selective and may generate perhalo compounds of the CFC type by dismutation, or are obtained from CFCs themselves by reduction methods, in practice by hydrogenolysis reactions. Thus, pentafluoroethane (F125) may be prepared by fluorination of perchloroethylene or of its intermediate fluorination products such as dichlorotrifluoroethane (F123) and chlorotetrafluoroethane (F124) or by hydrogenolysis of chloropentafluoroethane (F115). In both cases, the F125 produced contains non-negligible amounts of F115 which, since F115 is a CFC, should be removed as fully as possible.

Now, the existence of an F115/F125 azeotrope at 21% by weight of F115 (see U.S. Pat. No. 3,505,233) with a boiling point (−48.5° C. at 1.013 bar) which is very close to that of F125 (−48.1° C.) makes it virtually impossible to separate F115 and F125 completely by distillation. The F115 can thus only be removed from the F125 via a chemical route or by physical methods involving an intermediary substance.

In Patent Application EP 508,631, which describes the production of hydrofluorocarbons (HFC) by liquid-phase chemical reduction of chloro, bromo or iodo compounds with a metal hydride or a complex of such a hydride, it is indicated that this process may be advantageous for purifying certain HFCs such as F125. With the same aim, the Japanese patent application published (Kokai) under the No. 2001414/90 uses metal redox couples in a solvent medium. Other techniques, such as that described in Journal of Fluorine Chemistry, 1991 vol. 55, pp. 105–107, use organic reducing agents such as ammonium formate in DMF medium and in the presence of ammonium persulphate.

These processes, which use reactants that are difficult to handle (metal hydrides) or that are liable to pose effluent problems, are relatively incompatible with industrial production of F125 in large tonnage.

For the industrial manufacture of F125, the technique of extractive distillation appears to be an ideal process for removing the residual F115.

In an extractive distillation process, the constituents of a binary mixture are separated using a so-called extraction column containing successively, from the boiling vessel to the head, three sections, one for depletion, the second for absorption and the third for recovery.

The binary mixture to be fractionated is injected into the top of the depletion section, whereas the intermediary substance acting as selective solvent is introduced into the top of the absorption section so as to circulate in the liquid state from its point of introduction to the boiling vessel.

The third section, known as the recovery section, serves to separate out by distillation the constituent which is least absorbed from the traces of solvent entrained under the effect of its non-zero vapour pressure.

The application of this technique to the purification of 1,1,1,2-tetrafluoroethane (F134a) is the subject of U.S. Pat. No. 5,200,431; the extraction agent used is a chlorinated solvent or an aliphatic hydrocarbon.

The application of extractive distillation to the purification of F125 is already described in U.S. Pat. No. 5,087,329, which uses as extraction agent a $C_1$ to $C_4$ fluorohydrocarbon optionally containing hydrogen and/or chlorine atoms and having a boiling point of between −39 and +50° C. According to the data in that patent, the dichlorotetrafluoroethanes (F114 and F114a) are at least three times as effective as the other compounds mentioned. Moreover, 5 of the 8 solvents mentioned are CFCs forming the subject-matter of the Montreal protocol and whose marketing should cease in the near future.

The industrial use of the process according to that patent can therefore be envisaged economically only when the extraction agent used forms part of the chain of intermediates leading to F125, that is to say, in fact, in processes for the preparation of F125 by hydrogenolysis.

In the case of the manufacture of F125 by fluorination of perchloroethylene or of its partial fluorination products (F122, F123, F124), U.S. Pat. No. 5,087,329 only allows a choice between CFCs which will no longer be commercially available and products of lower performance such as F124 or F123.

DESCRIPTION OF THE INVENTION

It has now been found that perchloroethylene is of very much higher selectivity than chlorofluoroethanes and that there is also a wide settling range for F125/F115/perchloroethylene mixtures.

Settling of these mixtures makes it possible to obtain:
  a lower phase rich in perchloroethylene containing F125 enriched with F115 relative to the starting mixture of F125+F115 to be treated,
  an upper phase which is rich in F125 and depleted in F115 relative to the starting mixture of F125+F115 to be treated.

The F125/F115 ratio thus becomes established in the two phases in the following way:
  Upper phase>initial mixture>lower phase The subject of the present invention is thus a process for the purification of a pentafluoroethane containing chloropentafluoroethane by extractive distillation or by liquid/liquid extraction, characterized in that perchloroethylene is used as extraction agent.

The use of perchloroethylene as extraction solvent according to the invention is particularly advantageous to apply when it is desired to purify an F125 obtained by fluorination. The reason for this is that, in this case, the perchloroethylene used as extraction solvent is in fact the starting material used in the process for obtaining F125.

The process according to the invention may be carried out according to the well-known principles of extractive distillation or of liquid/liquid extraction, working under pressures of between 2 and 20 bar absolute, the temperatures being given by the liquid/vapour equilibrium diagrams of the individual constituents and of their mixtures.

BRIEF DESCRIPTION OF THE DRAWINGS

When the process is performed according to the scheme of FIG. 1 in an extractive distillation column, the charge (F125/F115 mixture to be separated) is injected via the pipe (1) at a point located at the head of the depletion section and the perchloroethylene, which is introduced into the column via pipe (2) at a point located at the head of the absorption section, circulates in the liquid state from its point of introduction to the boiling vessel. Purified F125 is removed at the head of the extractive distillation column via pipe (3) and perchloroethylene enriched in F115 is removed at the foot of the column via pipe (4).

The diameter and the number of stages in the extractive distillation column, the rate of reflux and the optimum temperatures and pressures may readily be calculated by a person skilled in the art from the data specific for the individual constituents and for their mixtures (relative volatilities, vapour pressures and physical constants).

Figure 1:
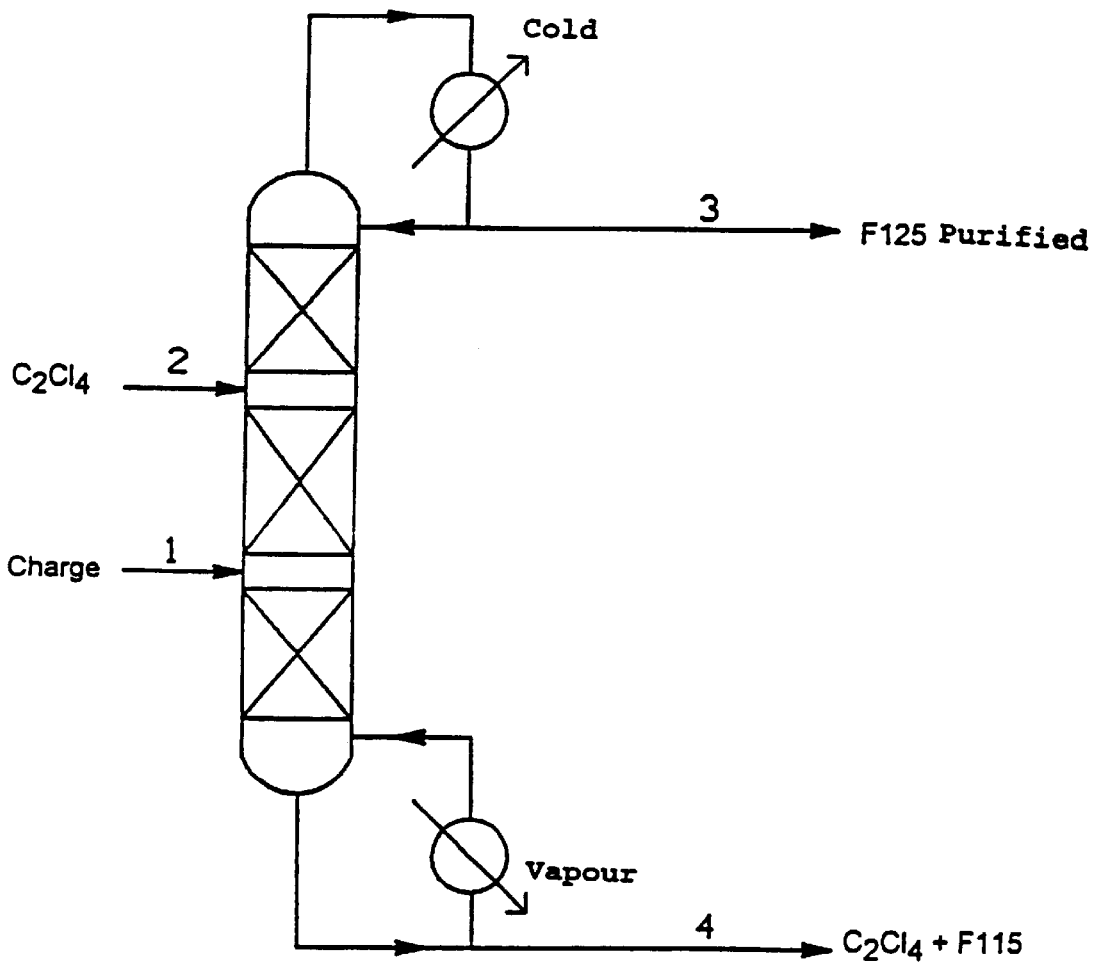
Figure 2:
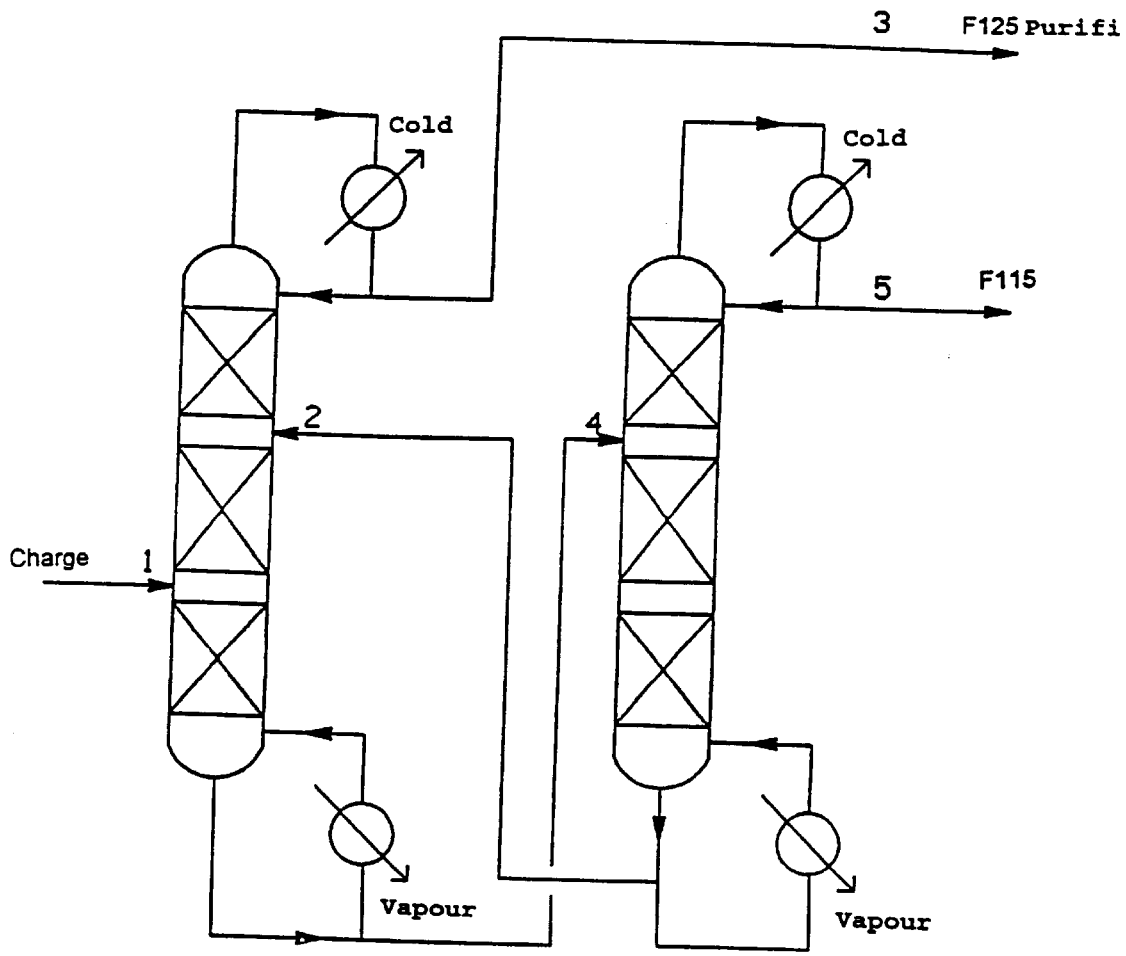

If it is desired to recycle the perchloroethylene, the device represented in FIG. 2 may be used, this device combining the extractive distillation column with a simple distillation column. The F115-enriched perchloroethylene leaving at the foot of the extractive distillation column is delivered via pipe (4) into the simple distillation column; the F115 is recovered at the head via pipe (5) and the perchloroethylene is recycled into the extractive distillation column via pipe (2).

F115 and F125 may be separated by liquid/liquid extraction with the aid of perchloroethylene according to any one of the standard techniques of liquid/liquid extraction known to those skilled in the art (extraction column, mixer/decanter in series, etc.).

EXAMPLES

The examples which follow illustrate the invention without limiting it.

Example 1

The ability of a solvent to be used in the separation of an F115/F125 mixture by extractive distillation is evaluated by means of its selectivity (S) defined as the ratio of the solubilities of F115 ($s_{115}$) and of F125 ($s_{125}$) in the solvent for the same partial pressure and the same temperature, i.e.

$$S = \frac{s_{115}}{s_{125}}$$

To determine these solubilities, a stainless-steel autoclave with a volume of 477.5 ml (for the comparative tests with F114) or a glass round-bottomed flask with a volume of 1052 ml (for the tests with perchloroethylene) is used. After the autoclave or the flask has been placed under vacuum, a partial pressure of F125, of F115 or of a gaseous mixture of F125+F115 of known composition is introduced therein. A known amount of solvent is then introduced by trapping or pouring in directly and the autoclave (or the flask) is placed in a chamber thermostatically adjusted to 25° C. After equilibrating, the total pressure is noted and a sample of the liquid phase and a sample of the gas phase are taken by means of a suitable device and are then analysed by gas chromatography.

The molar composition of the gas phase makes it possible to calculate the partial pressure of the F115 and/or of the F125. The solubility of the F115 ($s_{115}$) and of the F125 ($s_{125}$) in the solvent, expressed in g of F115 or of F125 per liter of solvent in the liquid phase, is calculated from the molar composition of the liquid phase.

Using F114 (for comparative purposes) or perchloroethylene (according to the invention) as solvent, the six tests summarized below were thus carried out.

Test A 333.3 mbar of F125

135.8 g of F114

Total pressure=2224 mbar at 25° C.

| | GAS PHASE | | LIQUID PHASE |
|---|---|---|---|
| | mol % | Partial pressure (mbar) | mol % |
| F125 | 4.6 | 102 | 0.49 |
| F114 | 95.4 | 2122 | 99.51 |

Solubility $s_{125}$=5.0 g/l

Test B 1000 mbar of F115

117.6 g of F114

Total pressure=2295 mbar at 25° C.

| | GAS PHASE | | LIQUID PHASE |
|---|---|---|---|
| | mol % | Partial pressure (mbar) | mol % |
| F125 | 9.46 | 217 | 2.15 |
| F114 | 90.54 | 2078 | 97.85 |

Solubility $s_{115}$=28.9 g/l

Test C 1000 mbar of gaseous mixture of F125+F115 containing 3.22 mol % of F115

140.4 g of F114

Total pressure=2394 mbar at 25° C.

| | GAS PHASE | | LIQUID PHASE |
|---|---|---|---|
| | mol % | Partial pressure (mbar) | mol % |
| F115 | 0.33 | 8 | 0.08 |
| F125 | 12.25 | 293 | 1.55 |
| F114 | 87.42 | 2093 | 98.37 |

Solubility $s_{115}$=1.1 g/l
Solubility $s_{125}$=16.1 g/l

Test D 1000 mbar of gaseous mixture of F125+F115 containing 10.0 mol % of F115

141.3 g of F114
Total pressure=2393 mbar at 25° C.

|  | GAS PHASE | | LIQUID PHASE |
|---|---|---|---|
|  | mol % | Partial pressure (mbar) | mol % |
| F115 | 0.91 | 22 | 0.21 |
| F125 | 11.09 | 265 | 1.42 |
| F114 | 88.00 | 2106 | 98.36 |

Solubility $s_{115}$=2.8 g/l
Solubility $s_{125}$=14.8 g/l
Test E
889 mbar of gaseous mixture of F125+F115 containing 9.86 mol % of F115
162 g of perchloroethylene
Total pressure=850 mbar at 25° C.

|  | GAS PHASE | | LIQUID PHASE |
|---|---|---|---|
|  | mol % | Partial pressure (mbar) | mol % |
| F115 | 8.58 | 73 | 0.15 |
| F125 | 89.82 | 763 | 0.46 |
| Perchloroethylene | 1.6 | 14 | 99.39 |

Selectivity $s_{115}$=2.2 g/l
Selectivity $s_{125}$=5.4 g/l
Test F
950 mbar of gaseous mixture of F125+F115 containing 3.2 mol % of F115
196 g of perchloroethylene
Total pressure=923 mbar at 25° C.

|  | GAS PHASE | | LIQUID PHASE |
|---|---|---|---|
|  | mol % | Partial pressure (mbar) | mol % |
| F115 | 2.68 | 25 | 0.047 |
| F125 | 94.21 | 870 | 0.54 |
| Perchloroethylene | 3.11 | 29 | 99.41 |

Selectivity $s_{115}$=0.7 g/l
Selectivity $s_{125}$=6.4 g/l

Figure 3:
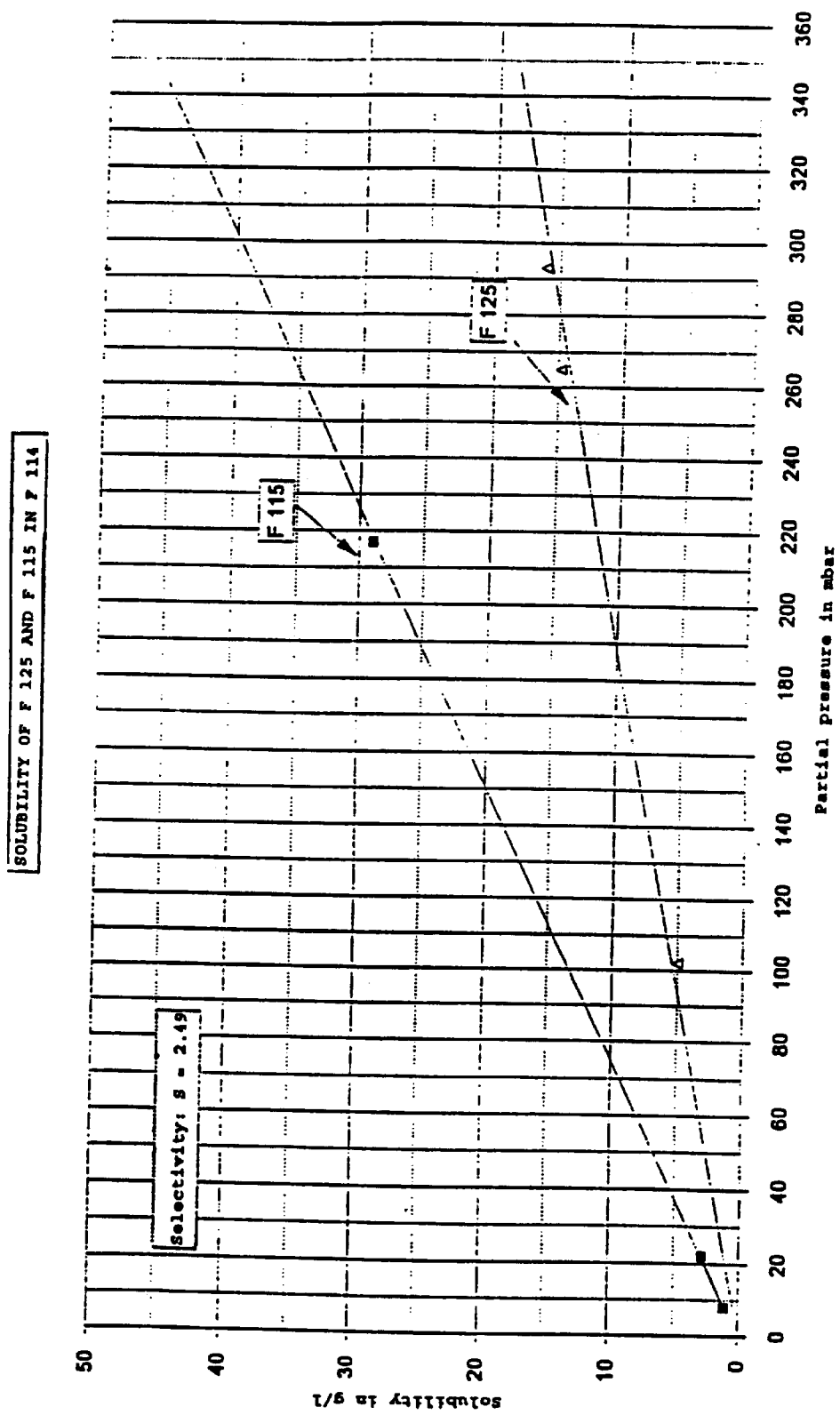
Figure 4:
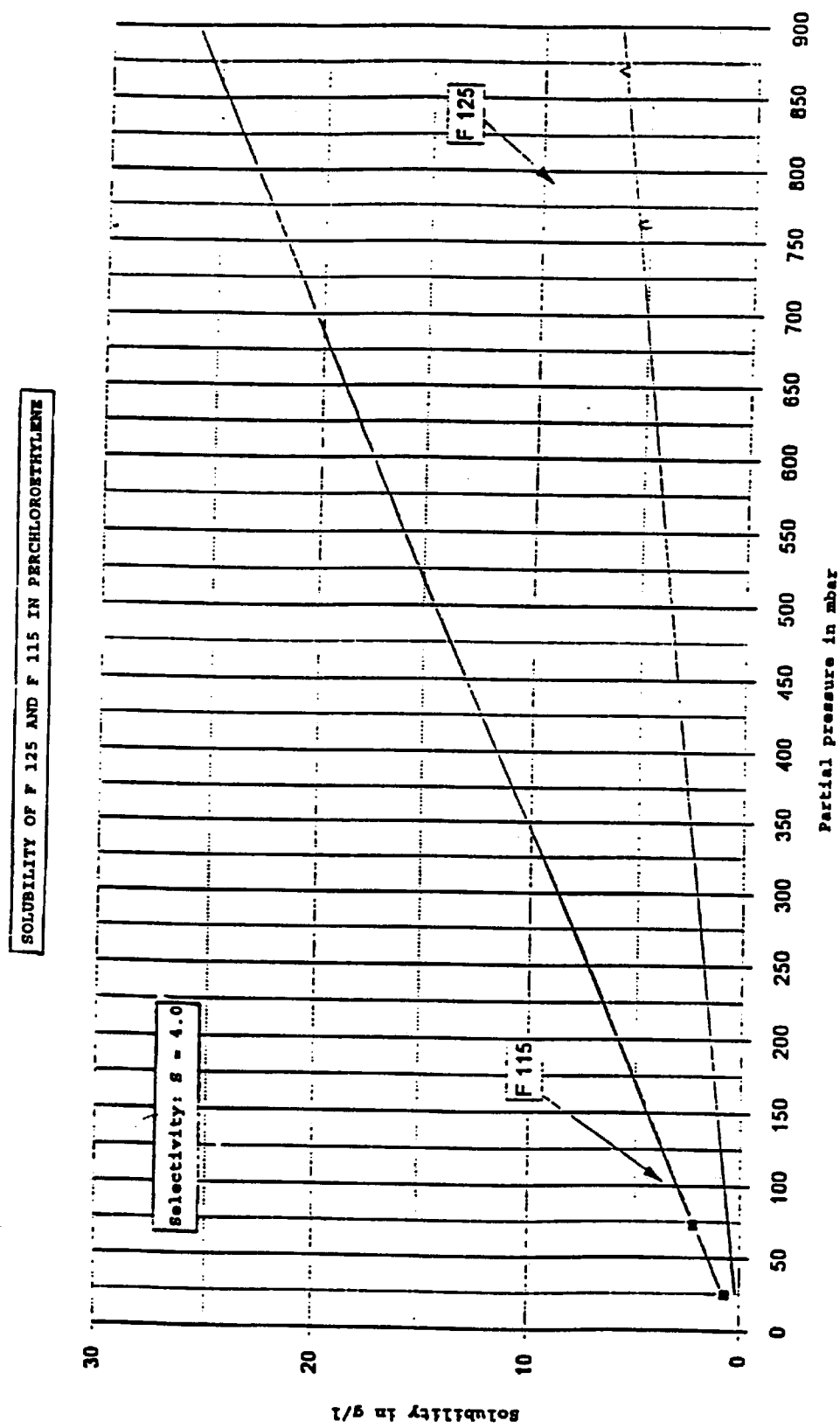

These tests made it possible to plot solubility curves for F125 and F115 in F114 (FIG. 3) and perchloroethylene (FIG. 4) as a function of the partial pressure of F125 and F115.

The selectivity obtained with F114 is 2.49 and is very much lower than that obtained with perchloroethylene (4.0).

Example 2

To determine the phase diagram of the F125/F115/perchloroethylene ternary mixture, a 204 ml stainless-steel autoclave fitted with two dip tubes allowing a sample of the two phases present to be taken is used.

After the autoclave has been placed under vacuum, a known amount of perchloroethylene is introduced, followed by an F125/F115 mixture of known composition, by trapping or pouring in directly. The autoclave is then placed in a chamber thermostatically adjusted to the desired temperature and, after equilibrating, the total pressure is noted and the composition of the two settled liquid phases present is analysed by gas chromatography. Two tests (G and H) were thus carried out and summarized in the following tables in which the percentages are expressed by weight.

Test G

| Temperature |  | +27.5° C. 12.3 |  |
|---|---|---|---|
| Pressure (bar abs) | Initial mixture | Upper phase | Lower phase |
| F125 | 49.73% | 80.10% | 11.98% |
| F115 | 2.74% | 4.23% | 0.95% |
| Perchloroethylene | 47.53% | 15.67% | 87.07% |
| F115/(F115 + F125) | 5.22% | 5.02% | 7.35% |
| F115/F125 | 5.51% | 5.28% | 7.93% |

Test H

| Temperature |  | +27.5° C. 12.3 |  |
|---|---|---|---|
| Pressure (bar abs) | Initial mixture | Upper phase | Lower phase |
| F125 | 24.16% | 29.11% | 10.91% |
| F115 | 35.66% | 40.91% | 19.79% |
| Perchloroethylene | 40.18% | 29.98% | 69.30% |
| F115/(F115 + F125) | 0.60% | 0.58% | 0.64% |
| F115/F125 | 1.48% | 1.41% | 1.81% |

Figure 5:
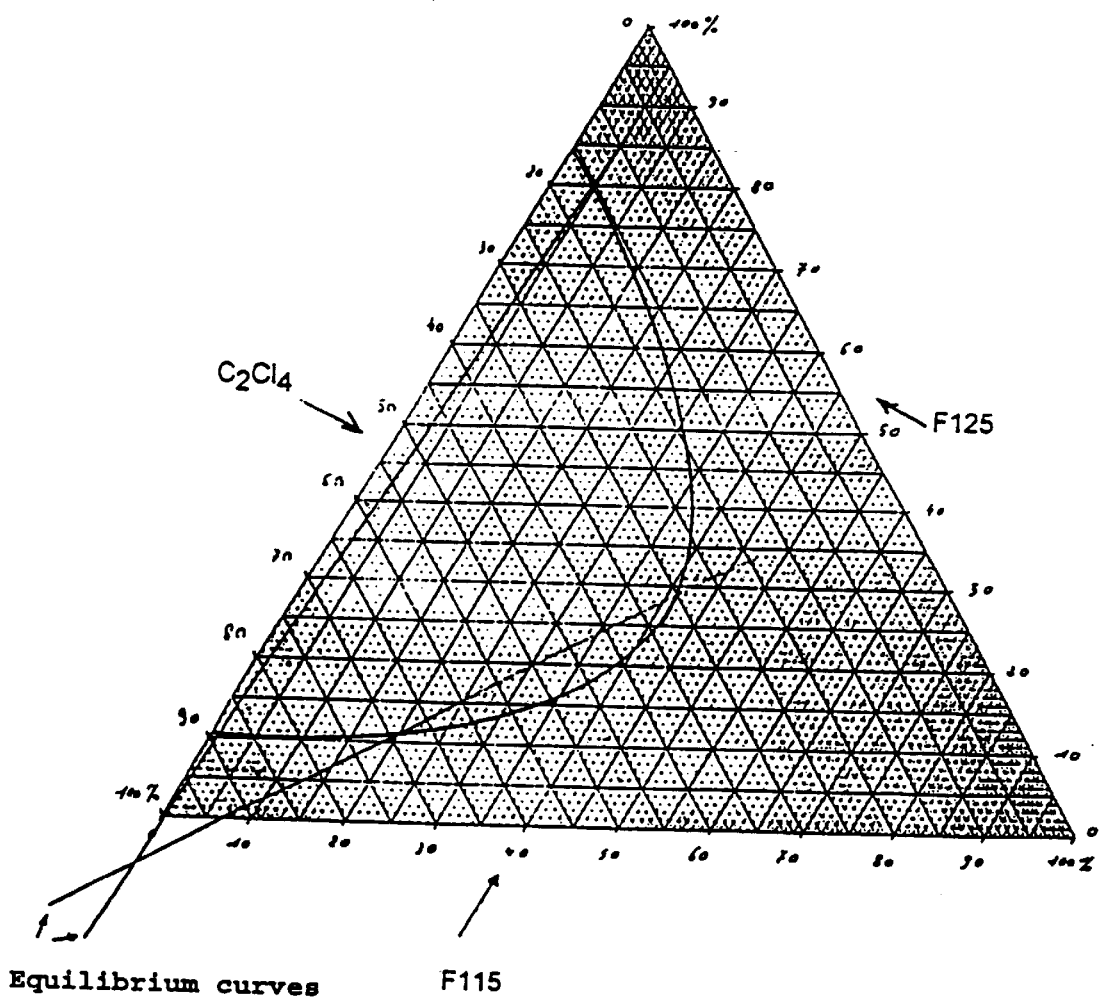

These tests, performed at 27.5° C., made it possible to plot the phase diagram of the F125/F115/perchloroethylene ternary mixture represented in FIG. 5.

Example 3

The following were circulated counter-currentwise in a counter-current liquid/liquid extraction column of 10 theoretical stages, operating at 27.5° C. and at 12.3 bar absolute:

436 kg/h of perchloroethylene
100 kg/h of a mixture of F125 (80% by weight) and F115 (20% by weight).
498.6 kg/h of extract containing most of the F115 and 37.4 kg/h of F115-depleted raffinate are obtained.

The material balance for the operation is summarized in the table below.

|  | Charge | | Perchloroethylene | | Extract | | Raffinate | |
|---|---|---|---|---|---|---|---|---|
|  | kg/h | wt % | kg/h | wt % | kg/h | wt % | kg/h | wt % |
| F125 | 80 | 80 | — | — | 50.1 | 10 | 29.9 | 80 |
| F115 | 20 | 20 | — | — | 18.1 | 4 | 1.9 | 5 |

-continued

| | Charge | | Perchloro-ethylene | | Extract | | Raffinate | |
|---|---|---|---|---|---|---|---|---|
| | kg/h | wt % | kg/h | wt % | kg/h | wt % | kg/h | wt % |
| $C_2Cl_4$ | — | — | 436 | 100 | 430.4 | 86 | 5.6 | 15 |
| TOTAL | 100 | — | 436 | — | 498.6 | — | 37.4 | — |

F125/(F125+F115) in the final mixture (raffinate)=94 wt %

What is claimed is:

1. Process comprising purification of a pentafluoroethane (F125) containing chloropentafluoroethane (F115) by liquid/liquid extraction or by extractive distillation, perchloroethylene is used as extraction agent.

2. Process according to claim 1, wherein it is carried out at a pressure of between 2 and 20 bar absolute.

3. A process for separating pentafluoroethane (F125) from a mixture of pentafluoroethane (F125) and chloropentafluoroethane (F115) comprising adding perchloroethylene as an extraction agent to the mixture, extractively distilling the mixture in an extractive distillation column, and recovering pentafluoroethane (F125) from the distillation column.

4. The process according to claim 3 wherein extractive distillation is carried out at a pressure of between 2 and 20 bar absolute.

* * * * *

UNITED STATES PATENT AND TRADEMARK OFFICE
CERTIFICATE OF CORRECTION

PATENT NO. : 6,307,115 B1
DATED : October 23, 2001
INVENTOR(S) : Emmanuel Guiraud et al.

It is certified that error appears in the above-identified patent and that said Letters Patent is hereby corrected as shown below:

<u>Title page,</u>
Item [73], please insert:
-- [73]  Assignee:      Elf Atochem S.A., Puteaux (FR) --

Signed and Sealed this

Twenty-fifth Day of May, 2004

JON W. DUDAS
*Acting Director of the United States Patent and Trademark Office*